US010772565B2

(12) United States Patent
Kahwash (10) Patent No.: US 10,772,565 B2
(45) Date of Patent: Sep. 15, 2020

(54) SYSTEMS AND METHODS FOR DELIVERING AN IMPLANTABLE DEVICE (71) Applicant: OHIO STATE INNOVATION FOUNDATION, Columbus, OH (US)

(72) Inventor: Rami Kahwash, New Albany, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 277 days.

(21) Appl. No.: 15/580,453

(22) PCT Filed: Jun. 10, 2016

(86) PCT No.: PCT/US2016/037037
§ 371 (c)(1),
(2) Date: Dec. 7, 2017

(87) PCT Pub. No.: WO2016/201336
PCT Pub. Date: Dec. 15, 2016

(65) Prior Publication Data
US 2018/0220970 A1 Aug. 9, 2018

Related U.S. Application Data (60) Provisional application No. 62/174,267, filed on Jun. 11, 2015.

(51) Int. Cl.
*A61B 5/0215* (2006.01)
*A61M 25/10* (2013.01)
(Continued)

(52) U.S. Cl.
CPC .......... *A61B 5/6853* (2013.01); *A61B 5/0215* (2013.01); *A61B 5/6876* (2013.01);
(Continued)

(58) Field of Classification Search
CPC .. A61M 25/1011–1015; A61F 2/95–97; A61F 2002/9505–9534;
(Continued)

(56) References Cited

U.S. PATENT DOCUMENTS 5,947,985 A 9/1999 Imram
6,485,500 B1 11/2002 Kokish et al.
(Continued)

OTHER PUBLICATIONS

Krejza et al. "Carotid Artery Diameter in Men and Women and the Relation to Body and Neck Size." Stroke. Apr. 2006;37(4):1103-5. Epub Feb. 23, 2006. (Year: 2006).*

(Continued)

*Primary Examiner* — Meredith Weare
(74) *Attorney, Agent, or Firm* — Meunier Carlin & Curfman LLC (57) ABSTRACT The delivery system may include, for example, an outer catheter having a distal tip and an inner support member, such as an inner catheter, disposed within the outer catheter. The inner support member includes an anchor member adjacent a distal tip of the inner support member and a support portion axially inward of the anchor member. The support portion is configured for supporting an implantable device thereon. A diameter of the anchor member corresponds to a diameter of a portion of a vessel in which the anchor member is to be disposed. The anchor member is configured to be lodged in the portion of the vessel to locate an intended position of the anchor member and to prevent movement of the inner support member relative to the vessel during release of the implantable device.

19 Claims, 5 Drawing Sheets (51) Int. Cl.
*A61B 5/00* (2006.01)
*A61M 25/04* (2006.01)

(52) U.S. Cl.
CPC .......... *A61B 5/6882* (2013.01); *A61B 5/6886* (2013.01); *A61M 25/04* (2013.01); *A61M 25/10* (2013.01); *A61B 5/0031* (2013.01); *A61B 2560/066* (2013.01); *A61M 2025/1015* (2013.01); *A61M 2025/1054* (2013.01)

(58) Field of Classification Search
CPC ...... A61F 2002/9583–9586; A61F 2002/9665; A61B 5/0215–02158; A61B 2560/063; A61B 2560/066
See application file for complete search history.

(56) References Cited

U.S. PATENT DOCUMENTS

| | | |
|---|---|---|
| 6,855,115 B2 | 2/2005 | Fonseca et al. |
| 7,966,886 B2 | 6/2011 | Corcoran et al. |
| 7,998,162 B2 | 8/2011 | Ho et al. |
| 8,353,841 B2 | 1/2013 | White et al. |
| 2001/0047184 A1 | 11/2001 | Conners |
| 2003/0204138 A1 | 10/2003 | Choi |
| 2005/0080346 A1* | 4/2005 | Gianchandani .......... B23H 9/00 600/486 |
| 2009/0030331 A1* | 1/2009 | Hochareon .......... A61B 5/0215 600/508 |
| 2012/0046560 A1 | 2/2012 | White et al. |
| 2012/0265283 A1 | 10/2012 | Mack et al. |
| 2013/0116549 A1 | 5/2013 | Gunday et al. |
| 2013/0253347 A1 | 9/2013 | Griswold et al. |
| 2013/0261544 A1 | 10/2013 | Hardin |
| 2014/0024955 A1* | 1/2014 | Zhadkevich ..... A61B 17/12045 600/486 |

OTHER PUBLICATIONS

European Patent Office. Extended European Search Report and Opinion. Issued in European Application No. 16808447.3 dated Jan. 15, 2019. 9 pages.

Abraham, William T., et al. "Wireless pulmonary artery haemodynamic monitoring in chronic heart failure: a randomised controlled trial." The Lancet 377.9766 (2011): 658-666.

International Search Report and Written Opinion of the International Searching Authority, PCT Application No. PCT/US2016/037037, dated Sep. 7, 2016, 10 pages.

* cited by examiner

SYSTEMS AND METHODS FOR DELIVERING AN IMPLANTABLE DEVICE

CROSS-REFERENCE TO RELATED APPLICATIONS

This application is a national stage application filed under 35 U.S.C. § 371 of PCT/US2016/037037 filed Jun. 10, 2016, which claims the benefit of U.S. Provisional Application Ser. No. 62/174,267, filed Jun. 11, 2015, the disclosures of which are hereby incorporated by reference in its entirety their entireties.

BACKGROUND

CARDIOMEMS, which is owned by St. Jude Medical, is a new FDA-approved device used for monitoring pulmonary artery pressures in patients with a history of systolic or diastolic heart failure and prior heart failure hospitalization within one year. The data from the device is transmitted wirelessly to a secure website and reviewed by health professionals. The sensor is very durable as it does not require a battery and does not have any moving parts. The sensor allows volume status of millions of patients worldwide to be managed more accurately and precisely. Various implementations of the CARDIOMEMS device are described in several U.S. patents, including U.S. Pat. Nos. 6,855,115, 7,966,886, and 8,353,841, which are incorporated by references in their entireties.

To deliver the CARDIOMEMS device to the left pulmonary artery, a guide wire and catheter are engaged in the left pulmonary artery using fluoroscopy, followed by obtaining an angiography of the left pulmonary branches. The branch of interest is located, and a picture of it is saved into the catheterization lab monitor. Then, the branch of interest is accessed with a delivery catheter over the wire. The device is deployed based on the assumption that the location has not changed.

Figure 1:
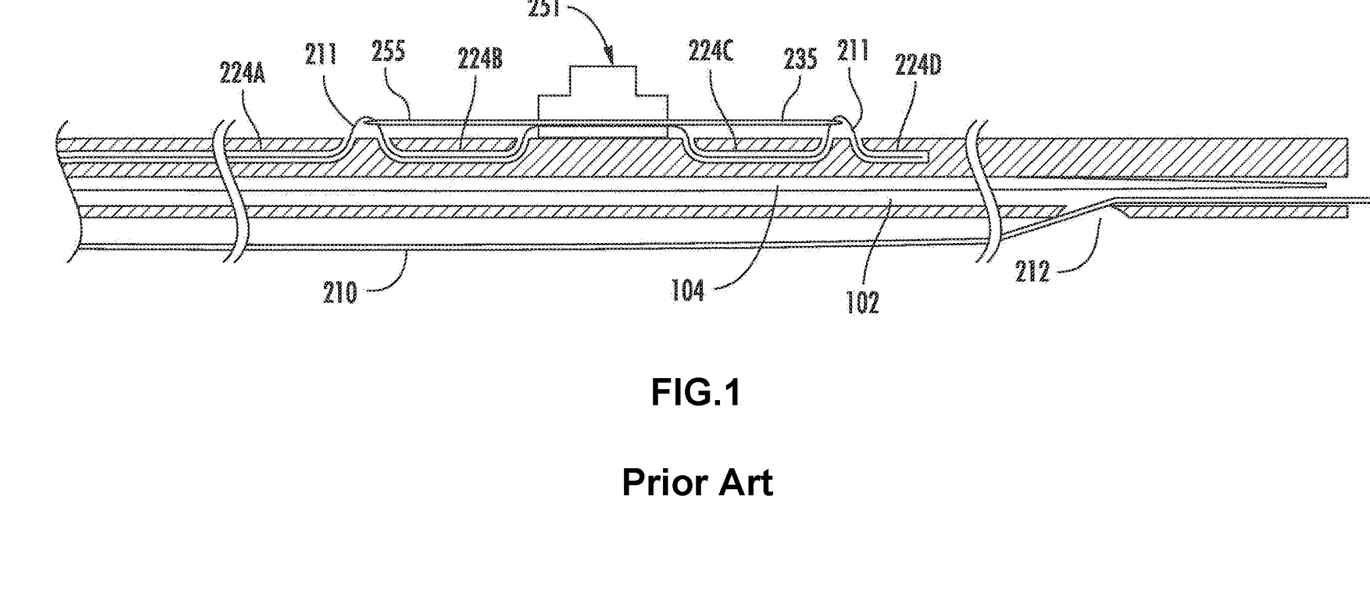
FIG. 1 illustrates a delivery apparatus for a CARDIOMEMS device according to the prior art.

For example, as described in U.S. Pat. No. 8,353,841, the CARDIOMEMS device may be delivered and deployed in its intended location in an artery using the delivery assembly shown in FIG. 1. The delivery assembly includes a main lumen 202 through which a core wire 204 is disposed and a secondary lumen having four sections 224A-224D through which a tether wire 211 is disposed. The tether wire 211 enters and exits the secondary lumen sections 224A-224D to attach wire loops 255, 235 of the CARDIOMEMS device 251 to the delivery assembly. The core wire 204 is fixed to the main lumen 202 and provides columnar stiffness to the delivery assembly, which facilitates advancement of the delivery assembly through the vasculature and prevents buckling of the delivery assembly when the tether wire is pulled proximally during deployment of the device 251. The main lumen 202 also includes a guide wire aperture 212 through which guide wire 210 extends into the main lumen 202. The delivery apparatus may be moved along the guide wire 210 through the artery in which the device 251 is to be deployed.

The lung is a very dynamic organ. For example, a wire within the left pulmonary artery may move 3 inches axially as the patient breathes. Therefore, establishing landmarks for delivering devices within the pulmonary artery can be very difficult. If the device is deployed distally of the branch of interest, the pressure waves are dampened. And, if the device is deployed proximally of the branch of interest, there is an increased risk that the device will dislodge in the main pulmonary artery, where it cannot be retrieved.

Accordingly, there is a need for an improved system and method for delivering an implantable device within a patient.

BRIEF SUMMARY

Described herein are various systems and methods of delivering an implantable device within a vessel of a patient. For example, in certain implementations, the delivery system includes an outer catheter having a distal tip and an inner support member disposed within the outer catheter. The inner support member includes an anchor member disposed adjacent a distal tip of the inner support member and a support portion axially inward of the anchor member. The support portion is configured for supporting an implantable device thereon. A diameter of the anchor member corresponds to a diameter of a portion of a vessel in which the anchor member is to be disposed. The anchor member is configured to be lodged in the portion of the vessel to locate an intended position of the anchor member and to prevent movement of the inner support member relative to the vessel during release of the implantable device.

In some implementations, the anchor member is a first anchor member, and the distal tip of the outer catheter includes a second anchor member. The second anchor member has a second diameter that corresponds to a second diameter of a portion of a second vessel in which the second anchor member is to be disposed. The first vessel and second vessel may be separate and adjacent arteries. For example, the first vessel may be a separate branch of the second vessel. Alternatively, the first vessel may be a distal, narrower portion of the second vessel.

In some implementations, the anchor members are inflatable balloons that have an inflated diameter. The inflated diameter of the first balloon is selected to lodge the first balloon in the portion of the vessel in which the first balloon is to be disposed. Similarly, the inflated diameter of the second balloon is selected to lodge the second balloon in the portion of the second vessel in which the second balloon is to be disposed. In certain implementations, the inflated diameter of the first balloon is smaller than the inflated diameter of the second balloon.

In addition, in some implementations, the inner support member may be an inner catheter.

According to certain implementations, the implantable device may include a hemodynamic sensor, such as, for example, the CARDIOMEMS sensor.

According to other various implementations; a method of delivering an implantable device within a body includes: (1) inserting a portion of a delivery system within a vessel of a patient, (2) extending a distal tip of an inner support member of the device past a distal tip of an outer catheter of the device such that an anchor member is outside of the outer catheter; (3) urging the anchor member through the vessel until the anchor member is lodged within the vessel; and (4) releasing the implantable device into a space within the vessel proximal of the anchor member. The delivery system may include one or more of the implementations described above.

The method may also include urging a second anchor member through a second vessel until the second anchor member is lodged within the second vessel after the first anchor member is lodged within the first vessel and prior to releasing the implantable device into the space between the first anchor member and the second anchor member.

In addition, the method may also include deflating the first inflatable balloon and retracting the distal tip of the inner support member into the outer catheter after releasing the implantable device and deflating the second inflatable balloon and retracting the outer catheter from the body after the distal tip of the inner support member has been retracted into the outer catheter.

BRIEF DESCRIPTION OF THE DRAWINGS

The components in the drawings are not necessarily to scale relative to each other. Like reference numerals designate corresponding parts throughout the several views.

DETAILED DESCRIPTION

Figures 2A, 2B:
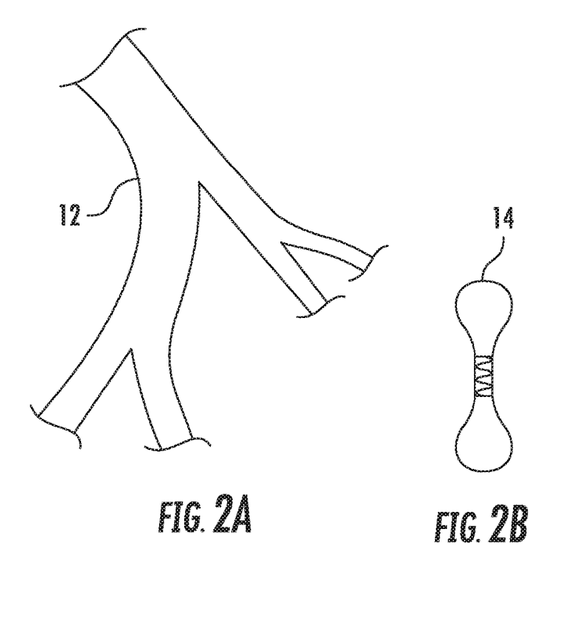
FIG. 2A illustrates branches in the left pulmonary artery.
FIG. 2B illustrates a hemodynamic sensor, according to one implementation.

Described herein are various systems and methods of delivering an implantable device within a vessel of a patient. For example, the device may be a hemodynamic sensor, such as a CARDIOMEMS sensor, and delivered to a portion of a patient's left pulmonary artery, according to certain implementations. A portion of the left pulmonary artery 12 is shown in FIG. 2A, and a hemodynamic sensor 14 is shown in FIG. 2B. However, other implementations may be configured for delivering other types of implantable devices, and those devices may be intended for other vessels within the patient's body.

The delivery system may include, for example, an outer catheter having a distal tip and an inner support member, such as an inner catheter, disposed within the outer catheter. The inner support member includes an anchor member adjacent a distal tip of the inner support member and a support portion axially inward of the anchor member. The support portion is configured for supporting an implantable device thereon. A diameter of the anchor member corresponds to a diameter of a portion of a vessel in which the anchor member is to be disposed. The anchor member is configured to be lodged in the vessel to locate an intended position of the anchor member and to prevent movement of the inner support member relative to the vessel during release of the implantable device.

Figure 3:
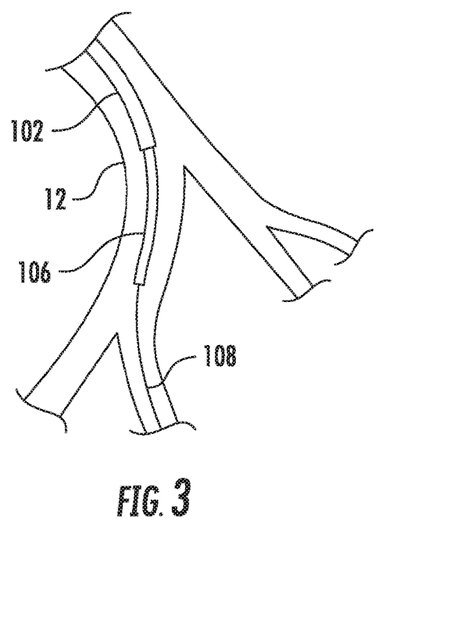
FIG. 3 illustrates a system for deploying the hemodynamic sensor shown in FIG. 2, according to one implementation.
Figure 4:
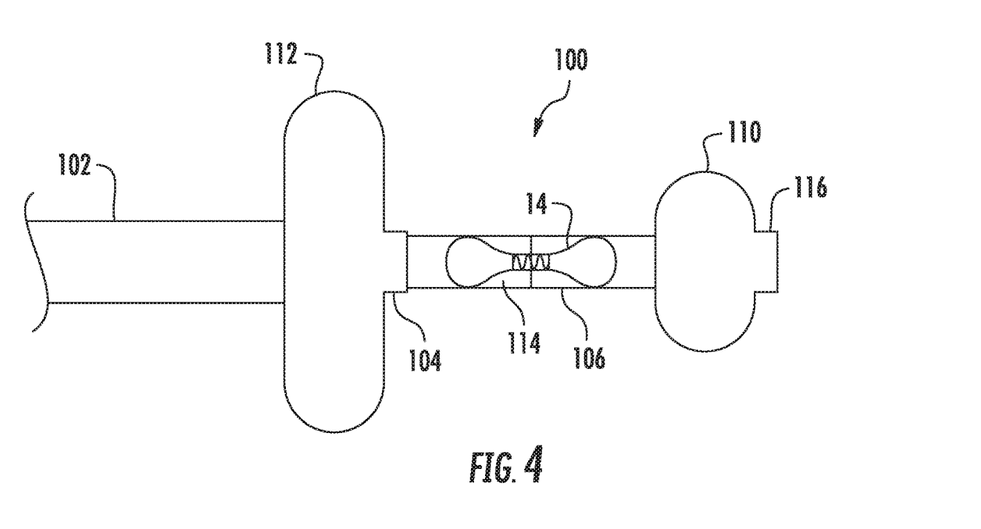
FIGS. 4-7 illustrate steps of deploying the hemodynamic sensor using the system shown in FIG. 3.
Figure 5:
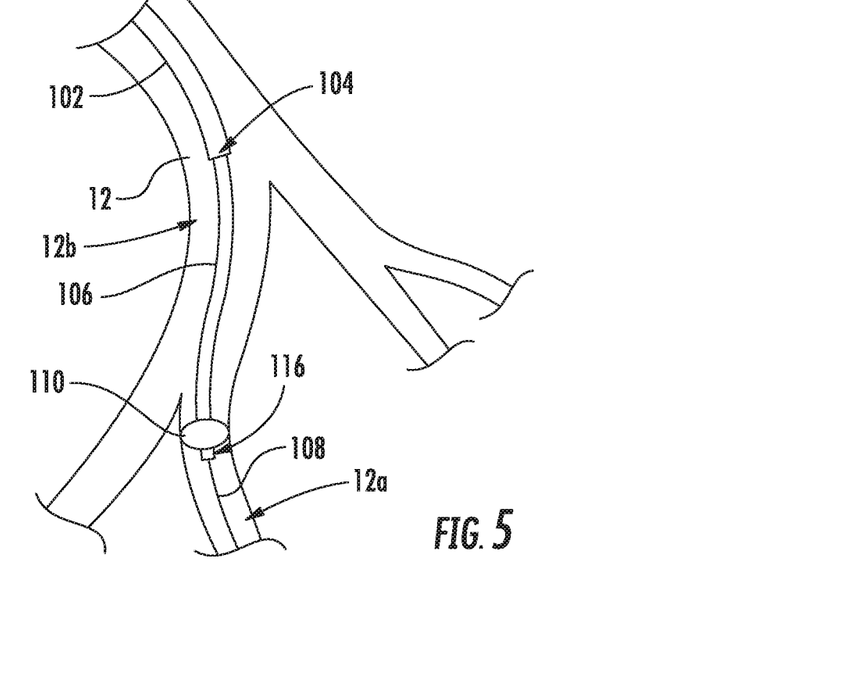

FIG. 3 illustrates a delivery system 100 according to one implementation. FIGS. 4-7 illustrate steps of deploying the hemodynamic sensor using the delivery system shown in FIG. 3. The delivery system 100 is shown in its extended, or delivery, position and includes an outer catheter 102 having a distal tip 104 and an inner support member 106 disposed within the outer catheter 102. The inner support member 106 may be an inner catheter according to some implementations. As shown in FIG. 4, the inner support member 106 includes an anchor member 110 disposed adjacent a distal tip 116 of the inner support member 106 and a support portion 114 axially inward of the anchor member 110. A diameter of the anchor member 110 corresponds to a diameter of a portion of a vessel in which the anchor member 110 is to be disposed, as shown in FIG. 5. The anchor member 110 is configured to be lodged in the portion of the vessel to locate an intended position of the anchor member 110 and to prevent movement of the inner support member 106 relative to the vessel during release of the implantable device.

Figure 6:
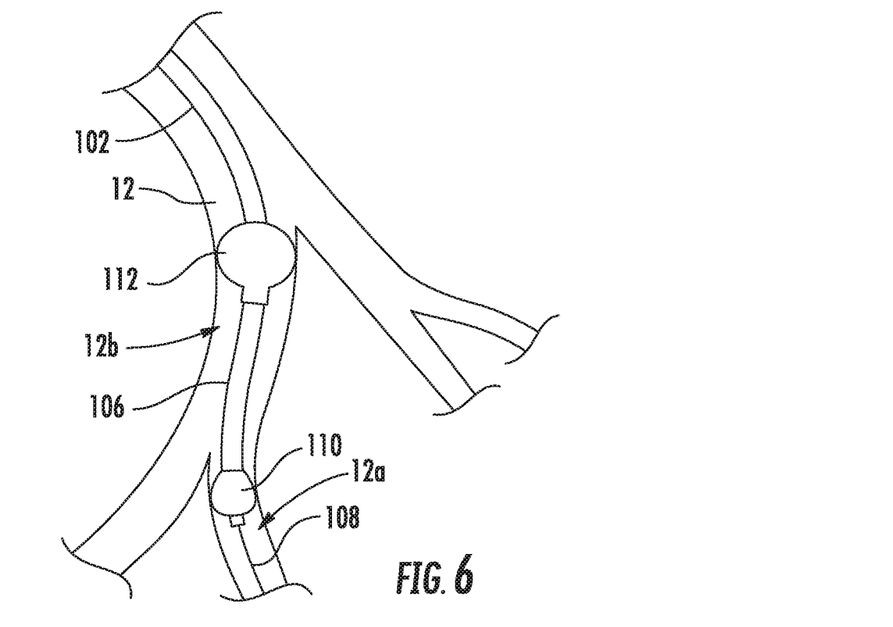

Referring to FIGS. 4 and 6, the system 100 also includes a second anchor member 112 at the distal tip 104 of the outer catheter 102. The second anchor member 112 has a second diameter that corresponds to a second diameter of a portion of a second vessel in which the second anchor member 112 is to be disposed. The second anchor member 112 is configured to be lodged in the portion of the vessel to locate an intended position of anchor member 112 and to prevent movement of the outer support member 102 relative to the vessel during release of the implantable device.

As shown in FIG. 4, the support portion 114 is configured for supporting an implantable device, such as hemodynamic sensor 14, thereon. For example, according to one implementation, the implantable device may be tied to the support portion 114, and during release, the surgeon may pull a string to release the implantable device within the vessel. However, other implementations may include other suitable types of coupling mechanisms to removably secure the implantable device to the support portion 114.

The first vessel and second vessel may be separate and adjacent arteries. For example, the first vessel may be a separate branch of the second vessel. Alternatively, the first vessel may be a distal, narrower portion of the second vessel.

In the implementation shown in FIG. 4, the anchor members 110, 112 are inflatable balloons that each have an inflated diameter. The inflated diameter of the first balloon 110 is selected to lodge the first balloon 110 in the portion of the vessel in which the first balloon is to be disposed. Similarly, the inflated diameter of the second balloon 112 is selected to lodge the second balloon in the portion of the second vessel in which the second balloon is to be disposed. In other words, the expected diameters of the first and second vessels may be the respective inflated diameters of the first and second balloons. In certain implementations in which the second vessel 12b is larger than the first vessel 12a, such as when the device 14 is to be disposed adjacent a branch between vessels 12a, 12b, (as shown in FIG. 6) the inflated diameter of the first balloon is smaller than the inflated diameter of the second balloon. For example, the inflated diameter of the first balloon 110 may be around 7 mm, and the inflated diameter of the second balloon 112 may be around 15 mm, according to one implementation. According to some implementations, balloons allow the surgeon to control the size of the anchor and are less traumatic to the vessel than other anchoring mechanism. However, other suitable anchoring mechanisms may be used in other implementations.

According to one exemplary implementation in which hemodynamic sensor 14 is to be delivered within the left pulmonary artery branch, at least a portion of the system 100 is inserted within a vessel of a patient, as shown in FIG. 5. The system 100 may be inserted over a guide wire 108, for example. The distal tip 116 of the inner support member 106 is extended past the distal tip 104 of the outer catheter 102 such that anchor balloon 110 is outside of the outer catheter 102, which is also shown in FIG. 5. The first balloon 110 is inflated, and the balloon 110 is urged through vessel 12a until the balloon 110 is lodged within the vessel 12a, which is shown in FIG. 5. The second balloon 112 is then inflated and urged through a second vessel 12b until it is lodged within the second vessel 121), which is shown in FIG. 6.

Figure 7:
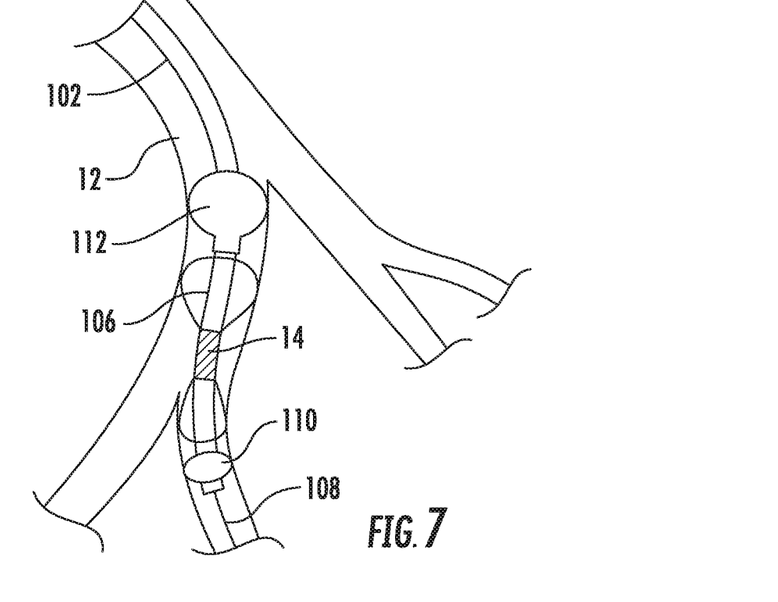

Then, the hemodynamic sensor 14 may be released into a space between the first balloon 110 and the second balloon 112, which is shown in FIG. 7.

Prior to releasing the hemodynamic sensor 14 within the left pulmonary artery branch, the strength of a signal from the sensor 14 may be tested by using a transceiver device (not shown) that is outside of the patient's body. The transceiver device is disposed on or near a patient's back adjacent the location of the sensor 14. If the signal received from the sensor 14 is sufficient, then the sensor 14 location is confirmed as being correct and the sensor 14 is released into the vessel. However, if the signal received from the sensor 14 is weak or inadequate, one or both of the balloons 110, 112 may be deflated to allow the support portion 114 and the sensor 14 to be moved to a more ideal location within the vessel. Once in the new position, the balloons 110, 112 are re-inflated and the signal strength of the sensor 14 is tested to confirm the placement of the sensor 14.

Figure 8:
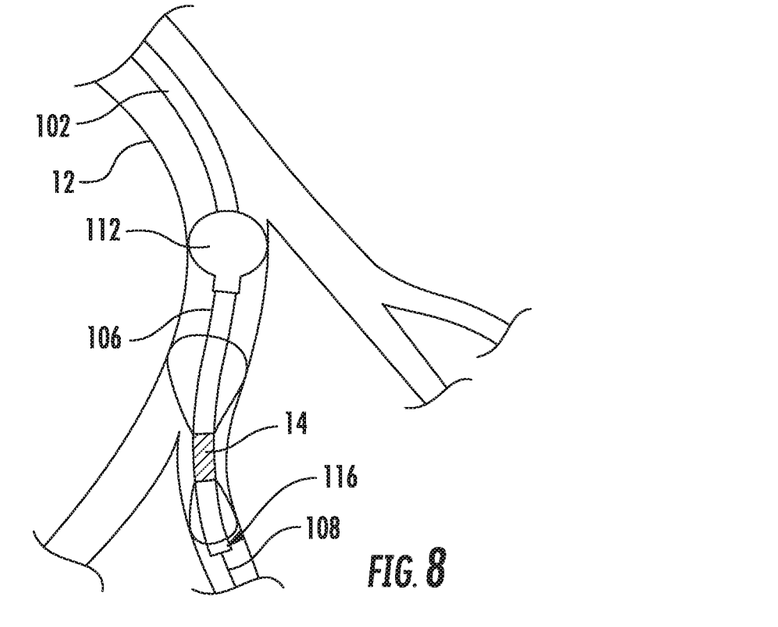
FIGS. 8-10 illustrates steps of retracting the system shown in FIG. 3 after the hemodynamic sensor is disposed in the intended position.
Figure 9:
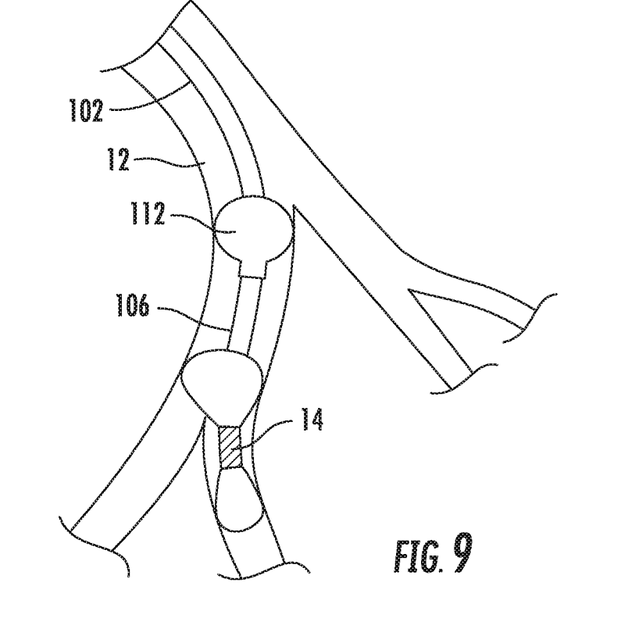
Figure 10:
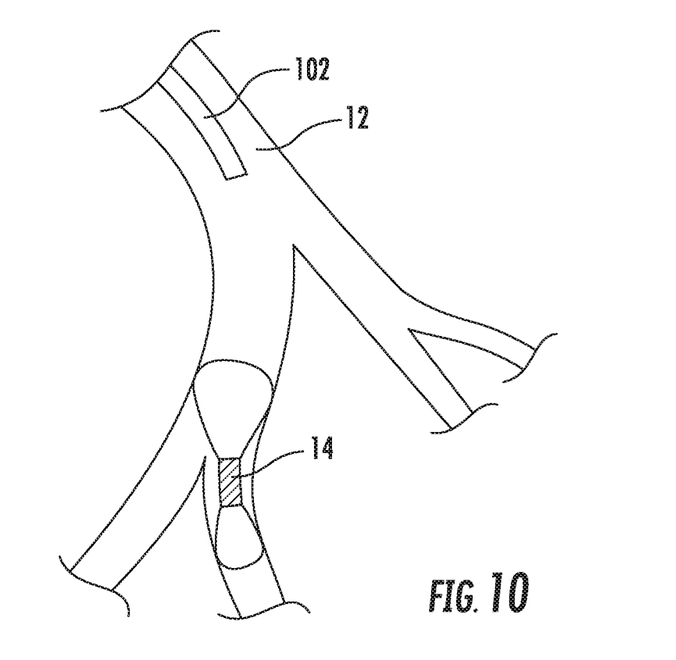

Once the hemodynamic sensor 14 is in its intended position, the delivery system 100 may be retracted. To retract the system 100, the first balloon 110 is deflated, which is shown in FIG. 8, and the distal tip 116 of the inner catheter 106 is retracted into the outer catheter 102, which is shown in FIG. 9. Then, the second inflatable balloon 112 is deflated, and the outer catheter 102 is retracted from the body, as shown in FIG. 10.

This system 100 and method of delivery of an implantable device within a vessel of a patient does not require catheter exchange over a guide wire or contrast dye, which is more efficient, less traumatic to the vasculature, has less side effects for the patient, and allows the surgeon to identify the best location for releasing the implantable device with minimal manipulations. For example, this system 100 may be used safely with patients having higher body mass, which are excluded from being subject to known delivery techniques.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. While implementations will be described for steering wheel hand detection systems, it will become evident to those skilled in the art that the implementations are not limited thereto.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting or layering arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present embodiments.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A delivery system configured for delivering an implantable device within the vasculature of a patient, the delivery system comprising:
   an outer catheter having a distal tip; and
   an inner support member disposed within the outer catheter, the inner support member comprising a first anchor member disposed adjacent a distal tip of the inner support member and a support portion axially inward of the first anchor member, the support portion comprising a coupling mechanism for coupling an implantable device to the inner support member, such that axial translation of the inner support member corresponds to simultaneous axial translation of the first anchor member, the support portion, and the coupling mechanism;
   wherein:
      a diameter of the first anchor member corresponds to a diameter of a portion of a first vessel in which the first anchor member is to be disposed,
      the first anchor member is configured to be lodged in the portion of the first vessel to locate an intended position of the first anchor member and to prevent movement of the inner support member relative to the first vessel during release of the implantable device, and the distal tip of the outer catheter comprises a second anchor member, the second anchor member having a second diameter corresponding to a second diameter of a portion of a second vessel in which the second anchor member is to be disposed.

2. The delivery system of claim 1, wherein the first anchor member is an inflatable balloon having an inflated diameter, wherein the inflated diameter is selected to lodge the balloon in the portion of the first vessel in which the balloon is to be disposed.

3. The delivery system of claim 1, wherein the first vessel and second vessel are separate and adjacent arteries.

4. The delivery system of claim 1, wherein the first vessel is a separate branch of the second vessel.

5. The delivery system of claim 1, wherein the first vessel is a distal, narrower portion of the second vessel.

6. The delivery system of claim 1, wherein:
the first anchor member is a first inflatable balloon having a first inflated diameter, wherein the first inflated diameter is selected to lodge the first balloon in the portion of the first vessel in which the first balloon is to be disposed, and
the second anchor member is a second inflatable balloon having a second inflated diameter, wherein the second inflated diameter is selected to lodge the second balloon in the portion of the second vessel in which the second balloon is to be disposed.

7. The delivery system of claim 6, wherein the first inflated diameter is smaller than the second inflated diameter.

8. The delivery system of claim 1, wherein the inner support member is an inner catheter.

9. The delivery system of claim 8, wherein the coupling mechanism comprises a string configured to secure the implantable device to the support portion.

10. The delivery system of claim 9, wherein the implantable device is a hemodynamic sensor.

11. A method of delivering an implantable device within a body, the method comprising:
inserting a portion of a delivery system within the vasculature of a patient, the delivery system comprising:
an outer catheter having a distal tip; and
an inner support member disposed within the outer catheter, the inner support member comprising a first anchor member disposed adjacent a distal tip of the inner support member and a support portion axially inward of the first anchor member, the support portion comprising a coupling mechanism for coupling an implantable device to the inner support member, such that axial translation of the inner support member corresponds to simultaneous axial translation of the first anchor member, the support portion, and the coupling mechanism;
wherein:
a diameter of the first anchor member corresponds to a diameter of a portion of a first vessel in which the first anchor member is to be disposed,
the first anchor member is configured to be lodged in the portion of the first vessel to locate an intended position of the first anchor member and to prevent movement of the inner support member relative to the first vessel during release of the implantable device, and
the distal tip of the outer catheter comprises a second anchor member, the second anchor member having a second diameter corresponding to a second diameter of a portion of a second vessel in which the second anchor member is to be disposed;
extending the distal tip of the inner support member past the distal tip of the outer catheter such that the first anchor member is outside of the outer catheter;
urging the first anchor member through the first vessel until the first anchor member is lodged within the first vessel;
urging the second anchor member through the second vessel until the second anchor member is lodged within the second vessel, and
releasing the implantable device into a space within the vasculature proximal of the first anchor member and between the first anchor member and the second anchor member.

12. The method of claim 11, wherein the first anchor member is an inflatable balloon having an inflated diameter, wherein the inflated diameter is selected to lodge the balloon in the portion of the first vessel in which the balloon is to be disposed, and the method further comprises inflating the inflatable balloon prior to urging the first anchor member through the first vessel.

13. The method of claim 11, wherein the first vessel and the second vessel are separate and adjacent vessels.

14. The method of claim 11, wherein:
the first anchor member is a first inflatable balloon having a first inflated diameter, wherein the first inflated diameter is selected to lodge the first balloon in the portion of the first vessel in which the first balloon is to be disposed, and
the second anchor member is a second inflatable balloon having a second inflated diameter, wherein the second inflated diameter is selected to lodge the second balloon in the portion of the second vessel in which the second balloon is to be disposed.

15. The method of claim 14, wherein the first inflated diameter is smaller than the second inflated diameter.

16. The method of claim 14, further comprising:
after releasing the implantable device, deflating the first inflatable balloon and retracting the distal tip of the inner support member into the outer catheter; and
deflating the second inflatable balloon and retracting the outer catheter from the body after the distal tip of the inner support member has been retracted into the outer catheter.

17. The method of claim 11, wherein the inner support member is an inner catheter.

18. The method of claim 17, wherein the coupling mechanism comprises a string configured to secure the implantable device to the support portion.

19. The method of claim 18, wherein the implantable device is a hemodynamic sensor.

* * * * *